United States Patent
Cardon et al.

(10) Patent No.: US 12,137,921 B2
(45) Date of Patent: *Nov. 12, 2024

(54) SURGICAL BONE PREPARATION INSTRUMENT AND ASSEMBLY COMPRISING SUCH AN INSTRUMENT

(71) Applicant: Tornier, Montbonnot-Saint-Martin (FR)

(72) Inventors: Jean-Emmanuel Cardon, Domene (FR); Christophe Magnac, Revel (FR)

(73) Assignee: TORNIER, Montbonnot-Saint Martin (FR)

( * ) Notice: Subject to any disclaimer, the term of this patent is extended or adjusted under 35 U.S.C. 154(b) by 396 days.

This patent is subject to a terminal disclaimer.

(21) Appl. No.: 17/566,929

(22) Filed: Dec. 31, 2021

(65) Prior Publication Data

US 2022/0125446 A1     Apr. 28, 2022

Related U.S. Application Data

(63) Continuation of application No. 16/259,528, filed on Jan. 28, 2019, now Pat. No. 11,234,717.

(30) Foreign Application Priority Data

Jan. 30, 2018   (EP) .................................. 18305086

(51) Int. Cl.
*A61B 17/16*      (2006.01)
*A61B 17/17*      (2006.01)
(Continued)

(52) U.S. Cl.
CPC ...... *A61B 17/1684* (2013.01); *A61B 17/1635* (2013.01); *A61B 17/1659* (2013.01);
(Continued)

(58) Field of Classification Search
CPC ..... A61B 17/1684; A61B 90/03; A61B 90/06; A61B 17/1635; A61B 17/1659;
(Continued)

(56) References Cited

U.S. PATENT DOCUMENTS 3,666,299 A   5/1972  Butler
5,047,035 A   9/1991  Mikhail
(Continued)

FOREIGN PATENT DOCUMENTS

CN   1359277 A     7/2002
CN   202202866 U   4/2012
(Continued)

OTHER PUBLICATIONS

First Examination Report issued in connection with corresponding Australian Patent Application No. 2019200582, Oct. 16, 2023, 3 pages.

(Continued)

*Primary Examiner* — Kevin T Truong
*Assistant Examiner* — Diana Jones
(74) *Attorney, Agent, or Firm* — DUANE MORRIS LLP

(57) ABSTRACT

This surgical bone preparation instrument (1) comprises a main body (5) terminated by a contacting surface (50) adapted to abut on a bone (B), and a sliding body (7) equipped with a cutting element (3) and which is movable in translation with respect to the main body (5). The bone preparation instrument (1) includes a cutting depth control ring (11) that is adjustable by a single hand, which forms an abutment surface (110) against the movement of one of the main body (5) and the sliding body (7) when the sliding body (7) reaches an adjusted cutting depth (D) corresponding to an adjustment position of the control ring (11).

15 Claims, 8 Drawing Sheets

(51) Int. Cl.
  *A61B 17/56* (2006.01)
  *A61B 90/00* (2016.01)
(52) U.S. Cl.
  CPC .............. *A61B 90/03* (2016.02); *A61B 90/06* (2016.02); *A61B 17/162* (2013.01); *A61B 17/17* (2013.01); *A61B 2017/568* (2013.01); *A61B 2090/034* (2016.02); *A61B 2090/036* (2016.02); *A61B 2090/062* (2016.02)
(58) Field of Classification Search
  CPC ........ A61B 2090/034; A61B 2090/036; A61B 17/162; A61B 17/17; A61B 2017/568
  See application file for complete search history.

(56) References Cited

U.S. PATENT DOCUMENTS

| | | | |
|---|---|---|---|
| 5,876,405 | A | 3/1999 | del Rio et al. |
| 6,383,188 | B2 | 5/2002 | Kuslich |
| 8,529,555 | B1 | 9/2013 | Ryll |
| 8,936,626 | B1 | 1/2015 | Tohmeh et al. |
| 10,857,005 | B2 | 12/2020 | Dassonville |
| 2001/0034526 | A1 | 10/2001 | Kuslich |
| 2003/0165791 | A1 | 9/2003 | Carmichael et al. |
| 2004/0073224 | A1 | 4/2004 | Bauer |
| 2007/0078483 | A1* | 4/2007 | Ewaschuk .............. A61B 17/29 606/205 |
| 2010/0161066 | A1 | 6/2010 | Iannotti et al. |
| 2012/0123420 | A1 | 5/2012 | Honiball |
| 2012/0150030 | A1 | 6/2012 | Reach, Jr. |
| 2014/0066933 | A1 | 3/2014 | Ek et al. |
| 2014/0276668 | A1 | 9/2014 | Ryll |
| 2015/0150688 | A1 | 6/2015 | Vanasse et al. |
| 2015/0190151 | A1 | 7/2015 | Budhabhatti et al. |
| 2016/0199151 | A1 | 7/2016 | Lantz |
| 2017/0143352 | A1* | 5/2017 | Papenfuss .......... A61B 17/1617 |
| 2017/0340458 | A1* | 11/2017 | Belcher ................ A61B 17/155 |

FOREIGN PATENT DOCUMENTS

| | | |
|---|---|---|
| CN | 103068328 A | 4/2013 |
| CN | 105342662 A | 2/2016 |
| CN | 105491975 A | 4/2016 |
| CN | 105496504 A | 4/2016 |
| CN | 106102602 A | 11/2016 |
| CN | 107530096 A | 1/2018 |
| KR | 20110138605 A | 12/2011 |
| WO | 2000013595 A1 | 3/2000 |
| WO | WO 00/13595 | 3/2000 |
| WO | 2013152102 A1 | 10/2013 |
| WO | WO 2013/152102 | 10/2013 |
| WO | 2015030652 A1 | 3/2015 |
| WO | WO 2015/030652 | 3/2015 |

OTHER PUBLICATIONS

First Office Action issued in connection with corresponding Chinese Patent Application No. 201910094017, Dec. 26, 2023, 12 pages.
Partial European Search Report issued in EP Application No. 18305086, dated Jul. 3, 2018, in 1 page.
European Search Report issued in EP Application No. 18305086.3, dated Oct. 23, 2018 in 11 pages.

* cited by examiner

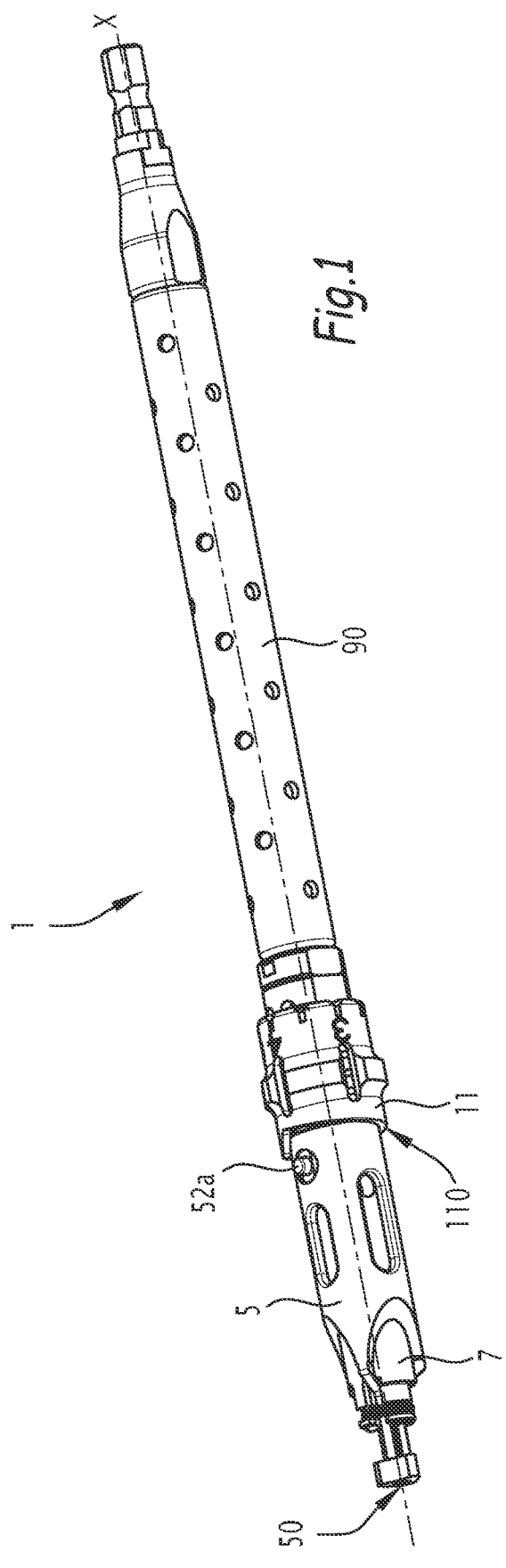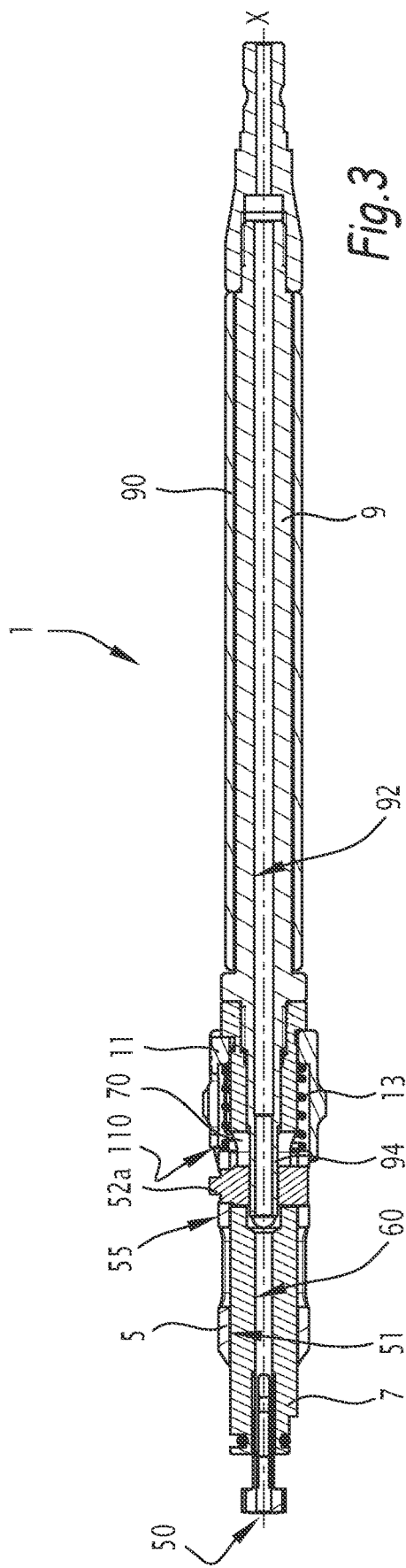

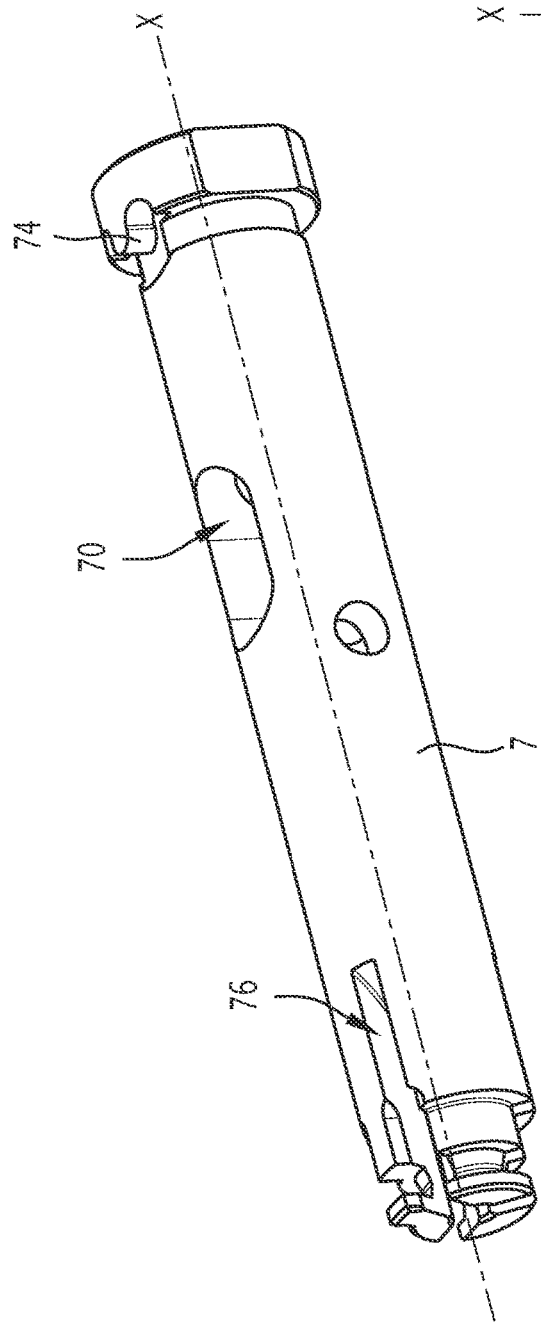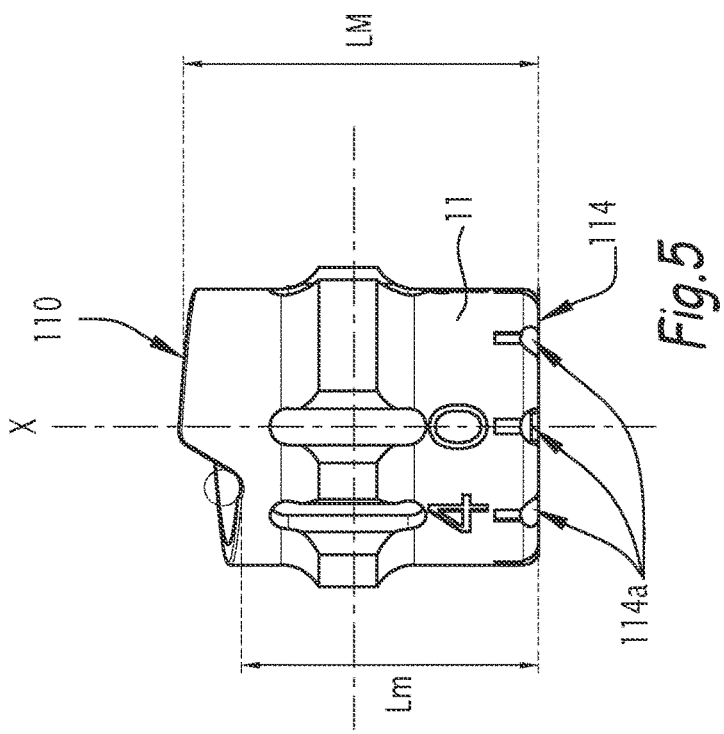

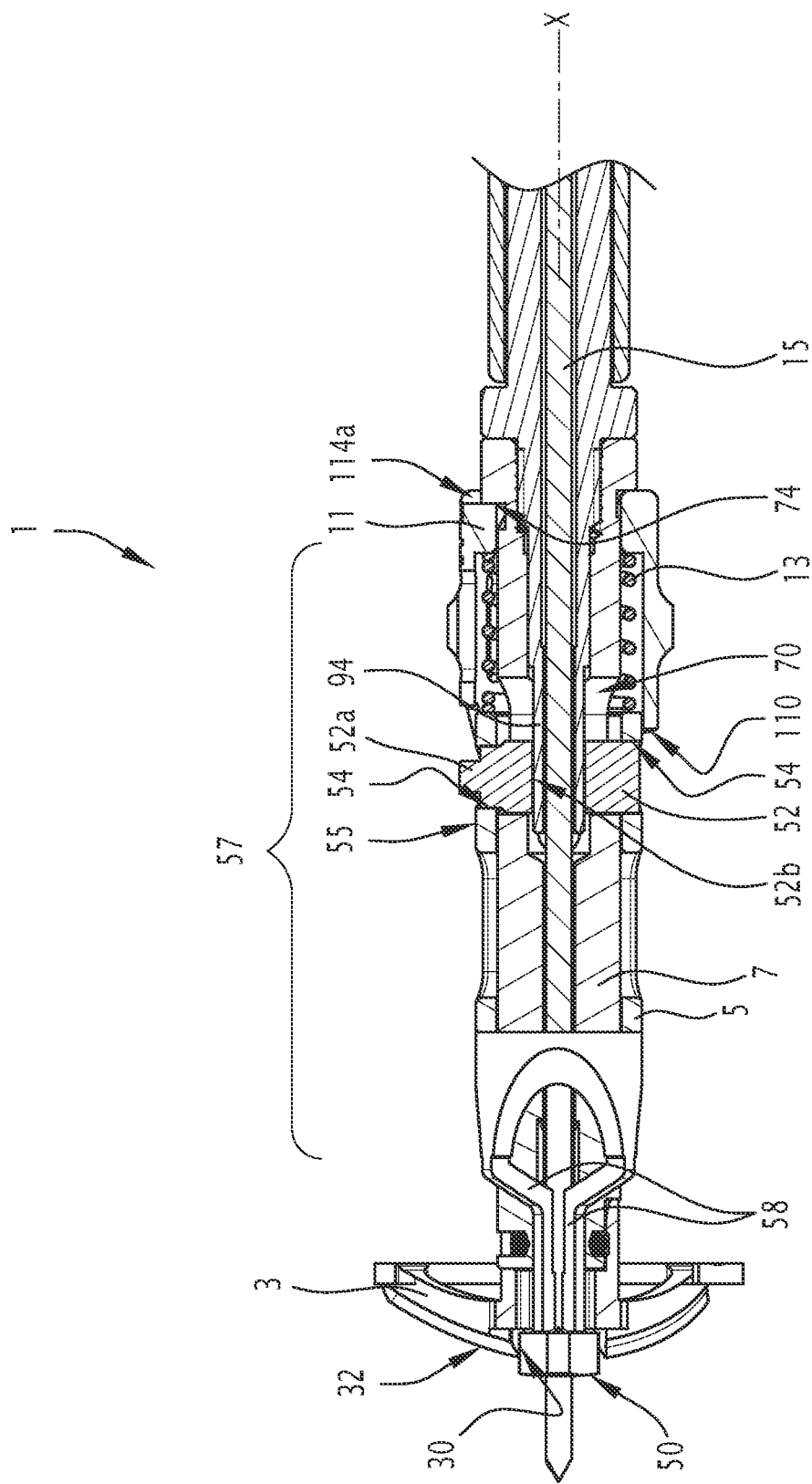

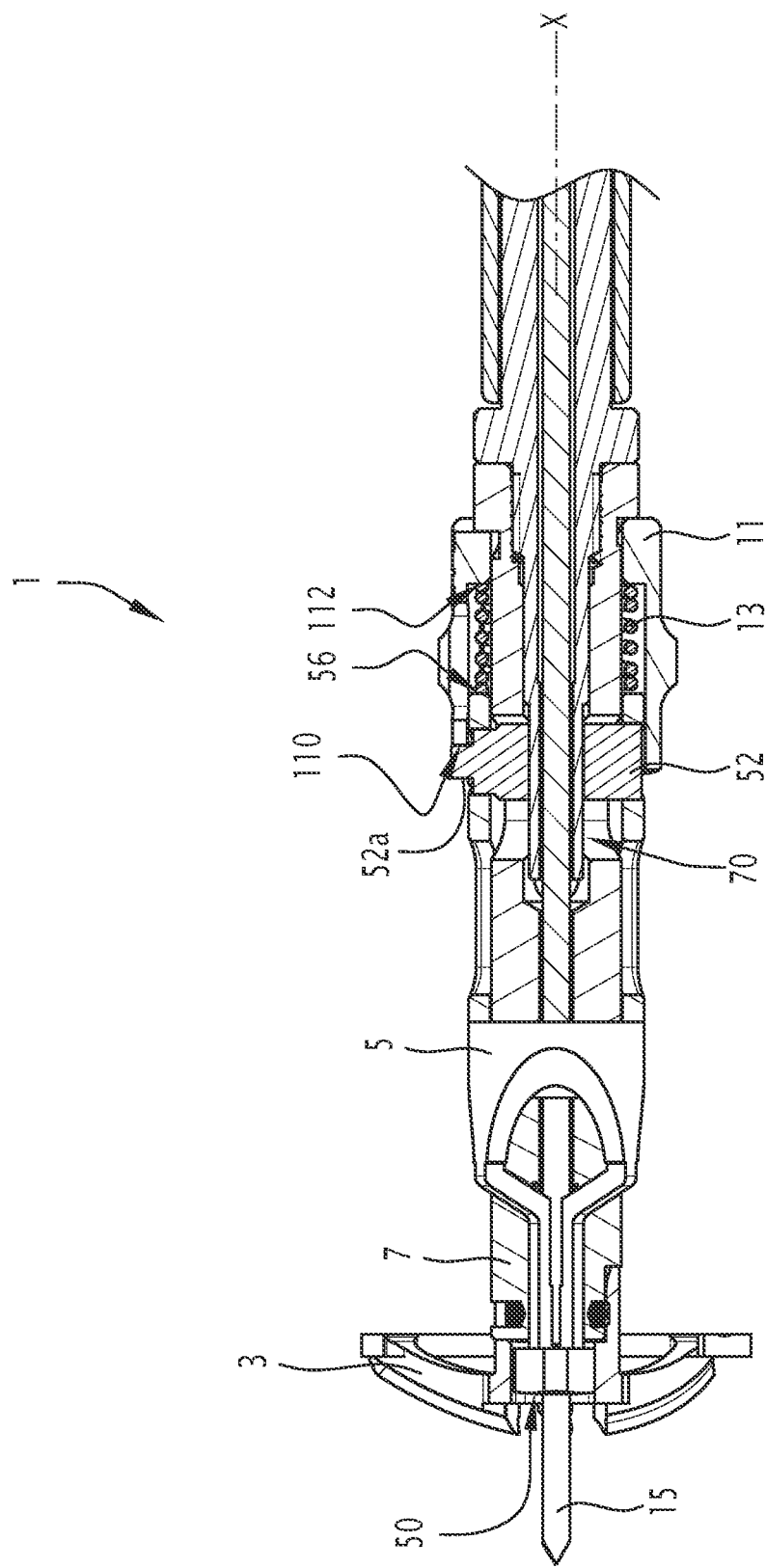

SURGICAL BONE PREPARATION INSTRUMENT AND ASSEMBLY COMPRISING SUCH AN INSTRUMENT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

The invention concerns a surgical bone preparation instrument and a surgical bone preparation assembly comprising such a surgical bone preparation instrument.

Description of the Related Art

The preparation of a surgical articulation replacement operation needs performing bone reaming to prepare the glenoid bone. This preparation consists of creating a space for receiving the implant. Such reaming must be done with a precise reaming depth determined on the basis of the features of the implant and the features of the bone of the patient.

To ensure that the reaming operation is done with the correct reaming depth, various techniques are already used. U.S. Pat. No. 6,277,121 provides a stop member mounted on a reaming instrument and whose position along the reaming instrument can be modified as a function of the required reaming depth. The stop member comprises a surface which abuts against a specific bushing attached to the bone when the desired reaming depth is reached.

Such technique needs further instruments to ensure that the desired reaming depth is correctly obtained.

SUMMARY OF THE INVENTION

The aim of the invention is to provide a new surgical bone preparation instrument, which allows controlling the reaming depth with the instrument itself.

To this end, the invention concerns a surgical bone preparation instrument comprising a main body terminated by a contacting surface adapted to abut on a bone, and a sliding body equipped with a cutting element and which is movable in translation with respect to the main body, wherein the bone preparation instrument includes a cutting depth control ring that is adjustable by a single hand, which forms an abutment surface against the movement of one of the main body and the sliding body when the sliding body reaches an adjusted cutting depth corresponding to an adjustment position of the control ring.

Thanks to the invention, the reaming depth can be controlled easily by setting an adjustment member of the instrument, which limits the relative translation of the main body and the sliding body of the instrument. The control of the reaming depth is therefore obtained with a simple blocking principle, and without the need of other instrument.

According to further aspects of the invention which are advantageous but not compulsory, such a surgical bone preparation instrument may also include one or several of the following features:

The cutting depth is adjusted by rotating the control ring to adjust the axial position of the abutment surface of the control ring with respect to the sliding body.

The cutting depth control ring is adjustable by a single action.

The main body comprises a radial pin extending in an oblong hole of the sliding body, the abutment surface of the cutting depth control ring acting as an axial stop on the radial pin.

The control ring comprises markings for checking the position of the control ring.

The cutting depth control ring is mounted on the sliding body with a screw mounting, and the cutting depth is adjusted by screwing or unscrewing the control ring to adjust its axial position on the sliding body.

The cutting depth control ring is mounted movable in rotation and fixed in translation on the sliding body and spring-biased by a spring with respect to the main body, and the abutment surface of the cutting depth control ring has a profile defining different axial lengths of the cutting depth control ring.

The spring urges the contacting surface of the main body against the bone during cutting.

The cutting depth control ring comprises a proximal axial surface having notches distributed circumferentially for positioning according to various depths corresponding to the different axial lengths of the control ring, and the sliding body comprises a protrusion adapted to insert in the notches of the proximal axial surface to lock the angular position of the control ring under action of the spring.

The sliding body is arranged radially inside a cylindrical portion of the main body, the contacting surface of the main body is arranged radially inside the cutting element, and the sliding body comprises longitudinal slits receiving in sliding manner attachment members of the main body which connect the contacting surface to the cylindrical portion.

The cutting element comprises a central aperture through which the contacting surface of the main body protrudes.

The sliding body can be dismounted from the main body.

The adjusted cutting depth is pre-planned.

The main body and the sliding body comprise a bore for insertion of a reference pin adapted to be fixed to the bone in order to guide the bone preparation instrument.

The invention also concerns a surgical bone preparation assembly comprising a surgical bone preparation instrument according to any of the preceding claims, wherein it comprises at least one reference pin adapted to be fixed to a bone to be prepared of a patient in order to guide the bone preparation instrument, and wherein it comprises a patient-specific positioning tool for positioning the reference pin on the bone.

BRIEF DESCRIPTION OF THE DRAWINGS

The invention will now be explained in correspondence with the annexed figures, as an illustrative example. In the annexed figures:

FIG. 1 is a perspective view of a surgical bone preparation instrument according to a first embodiment of the invention, a cutting element being omitted;

FIG. 3 is a sectional view of the instrument of FIGS. 1 and 2, along a longitudinal plane comprising a central axis of the instrument, the cutting element being omitted;

FIG. 4 is a perspective view of a sliding body of the instrument of FIGS. 1 to 3;

FIG. 5 is a side view of a control ring of the instrument of FIGS. 1 to 3;

FIG. 6 is a sectional view of the instrument of FIGS. 1 to 3, prior to a cutting step;

FIG. 7 is a sectional view similar to FIG. 6, at the end of a cutting step;

DETAILED DESCRIPTION OF THE PREFERRED EMBODIMENT

Figure 2:
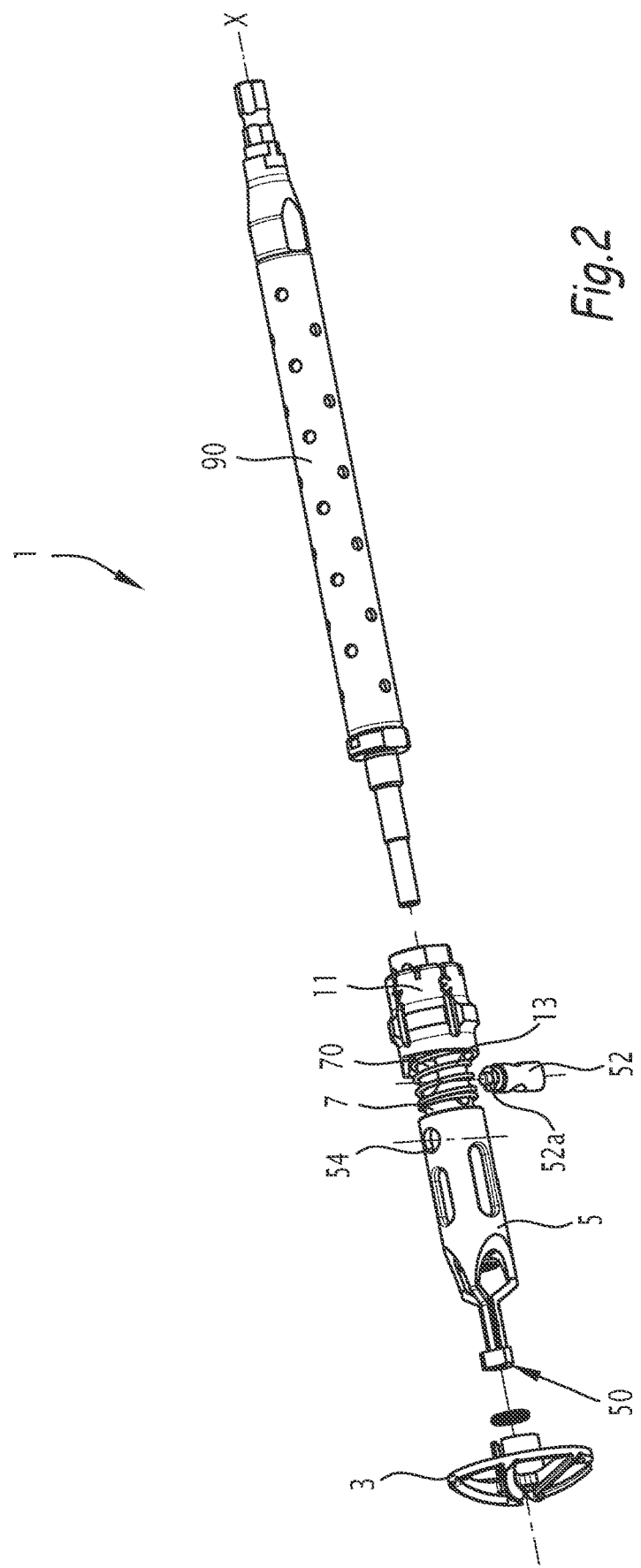
FIG. 2 is a partially exploded perspective view of the instrument of FIG. 1 with the cutting element being shown.
Figure 8:
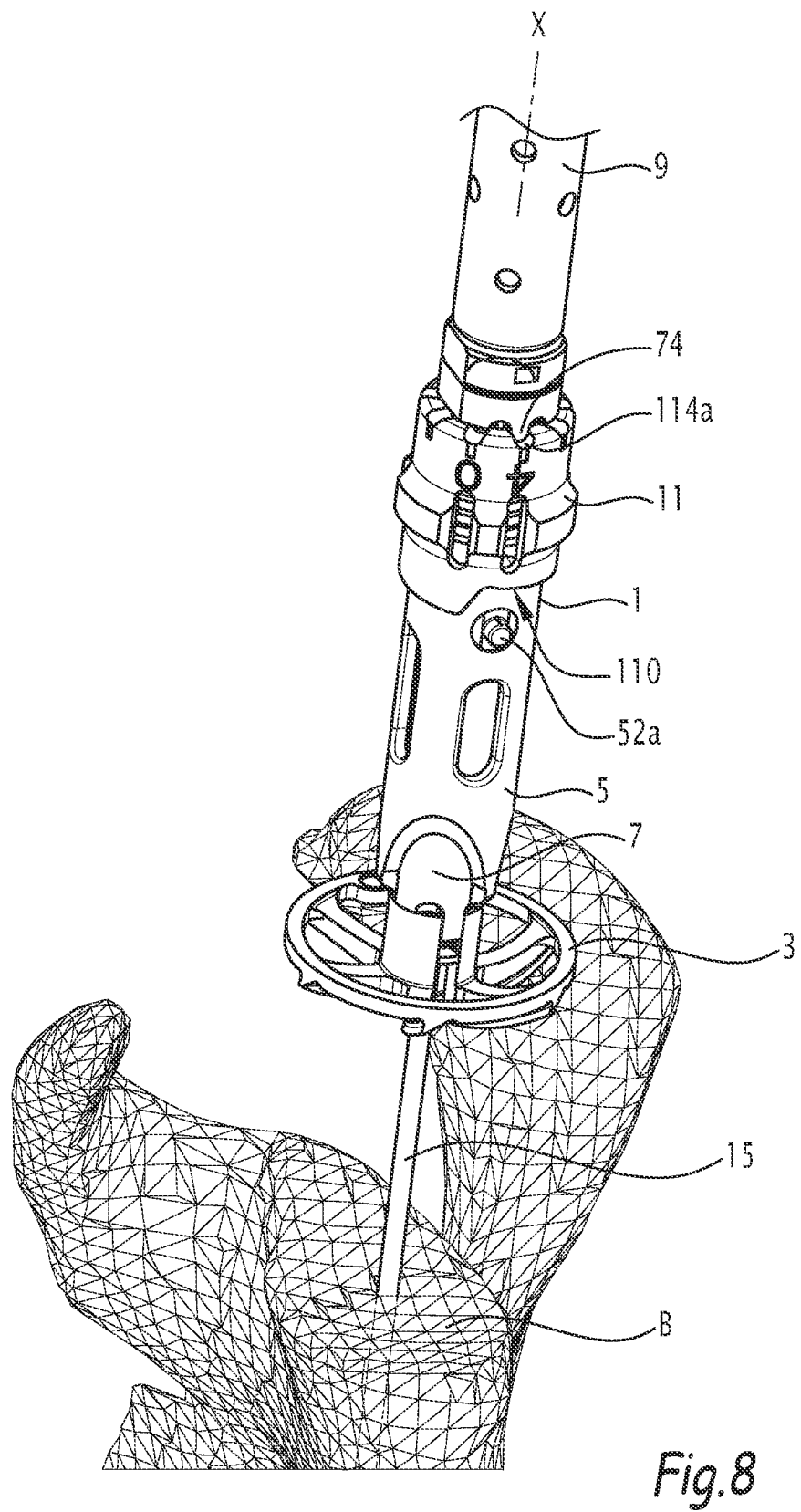
FIG. 8 is a perspective view of the instrument of FIG. 1, of a reference pin on which the instrument is mounted, and a bone in which the reference pin is attached, the instrument being represented prior to a cutting step.

FIGS. 1 to 3 represent a surgical bone preparation instrument 1 which extends along a central axis X. The axis X also corresponds to the translation axis of the instrument 1 during the reaming of a glenoid surface for a bone preparation prior to a surgical articulation replacement operation.

The instrument 1 comprises a reaming tool 3 which is fixed on the instrument 1. The central axis X is also the rotation axis of the reaming tool 3.

The instrument 1 comprises a main body 5 terminated by a contacting surface 50 adapted to abut on a bone B which is to be prepared using the instrument 1. The contacting surface 50 is substantially orthogonal to the central axis X.

In what follows, the term "distal" denotes an element of the instrument 1 located on the side of the contacting surface 50 or a surface oriented towards the contacting surface 50. The term "proximal" denotes an element of the instrument 1 located opposite the contacting surface 50 or a surface oriented opposite to the contacting surface 50. The forward direction is oriented towards the distal side.

The terms "axial" or "axially" and "radial" or "radially" refer respectively to directions parallel and transverse to the central axis X. An axial surface is a surface orthogonal to the central axis X, while a radial surface is a cylindrical surface centered on the central axis X.

The main body 5 is hollow and forms an inner cavity 52 in which is inserted a sliding body 7, that is equipped with the reaming tool 3. Alternatively, the sliding body 7 may be equipped with another type of cutting element. The sliding body 7 is movable in translation with respect to the main body 5 along the central axis X.

The instrument 1 also comprises an elongated handle 9 that extends axially from the sliding body 7. The handle 9 is covered by a perforated sleeve 90.

During the reaming of a surface of the bone B, the surface 50 abuts the bone B and remains stationary, while the sliding body 7 moves along the axis X with respect to the main body 5 and progressively reams the bone B. To control the reaming depth, the axial displacement of the sliding body 7 with respect to the main body 5 must be limited to a predefined value corresponding to the desired reaming depth.

To this end, the instrument 1 comprises a cutting depth control ring 11. The control ring 11 is adjustable by a single hand. The control ring 11 forms an abutment surface against the axial movement of one of the main body 5 and the sliding body 7 when the sliding body 7 reaches an adjusted cutting depth corresponding to an adjustment position of the control ring 11.

The control ring 11 is rotatable with respect to the main body 5 and the sliding body 7, and movable in translation with respect to the main body 5 so as to be set to the adjustment position corresponding to the desired cutting depth. The control ring 11 comprises a distal surface 110 that forms the abutment surface. The main body 5 comprises a radial pin 52 which is inserted in a through oblong hole 70 of the sliding body 7. The oblong hole 70 has a largest dimension oriented parallel to the central axis X, meaning that the pin 52 is free to move in translation in the oblong hole 70 along the axis X. The pin 52 is also inserted into two opposed holes 54 of the main body 5. The holes 54 have a shape corresponding to the outer shape of the pin 52, meaning that the pin 52 is stationary in translation along the central axis X with respect to the main body 5. The pin 52 comprises a radial protrusion 52a which protrudes from an outer peripheral surface 55 of the main body 5. The protrusion 52a faces the distal surface 110 of the control ring 11 and acts as a stop to block the sliding body 7 to the depth corresponding to the adjusted position of the control ring 11.

The control ring 11 is mounted on the sliding body 7 with a spring 13 that urges the control ring 11 towards the proximal side of the instrument 1. The spring 13 is mounted between an axial surface 56 of the main body 5, and an inner axial surface 112 of the control ring 11.

The control ring 11 comprises a proximal axial surface 114 having notches 114a which are distributed circumferentially for positioning the control ring 11 according to various adjusted positions defining cutting depths which correspond to different axial lengths of the control ring 11. As represented on FIG. 5, the various notches 114a define, with respect to the abutting surface 110, various axial lengths of the control ring 11 depending on their position around the central axis X. The abutting surface 110 has a substantially helical profile defining increasing cutting depths from a first adjusted position "0" which defines a zero cutting depth, to a last adjusted position "4", which defines a maximal cutting depth. The control ring 11 comprises engraved markings or other types of markings showing the cutting depth associated with each of the notches 114a. The minimal cutting depth "0" corresponds to a maximal axial length LM of the control ring 11, while the maximal cutting depth "4" corresponds to a minimal axial length Lm of the control ring 11.

The markings of the control ring 11 can be different, designing different depths and different incremental values. The positioning of the notches 114a along the circumferential direction of the control ring 11, the preset depths of the control ring 11 and the maximal and minimal axial lengths LM and Lm can be different, and may be modified depending on the types of surgical procedures and patient geometries.

The sliding body 7 comprises a protrusion 74 located at the proximal side of the sliding body 7 and oriented towards the distal side, which has a shape complementary to the shape of the notches 114a. The protrusion 74 is adapted to insert in the notches 114a to lock the angular position of the control ring 1 under action of the spring 13. When the protrusion 74 is engaged in one of the notches 114a, the axial position of the control ring 11 is locked by the abutment between the protrusion 74 and the notch 114a under action of the spring 13. At the same time, the round shape of the protrusion 74 and the notch 114a prevents relative rotation of the control ring 11 with respect to the sliding body 7, locking the adjusted position of the control ring 11 and the desired cutting depth. If the desired cutting depth is to be modified, the control ring 11 has to be pushed forward by hand to release the notch 114a from the protrusion 74, then turn the control ring 11 around the central axis X to position the control ring 11 so that the protrusion 74 is aligned with another of the notches 114a according to the new desired cutting depth. This can be done with a single movement of two fingers of a single hand. The adjustment of the control ring 11 needs only one action. In other words, the surgeon only needs to place its fingers on the control ring 11 and make the movement. There is no need for displacing the fingers in another position to perform another movement.

Simultaneously, the spring 13 also pushes forward the main body 5 by urging the main body 5 away from the control ring 11, which is in fixed axial relationship with the sliding body 7. The spring 13 therefore urges the contacting surface 50 against the bone B during cutting.

The sliding body 7 is arranged radially inside a cylindrical portion 56 of the main body 5. The contacting surface 50 is arranged radially inside the cutting element 3, the link between the cylindrical portion 56 and the contacting surface 50 is made by attachment members 58 that are received in longitudinal slits 76 of the sliding body 7. The slits 76 extend on the distal side of the sliding body 7 and allow the axial translation of the connecting members 58 along the axis X. The cutting element 3 comprises a central aperture 30 through which the contacting surface 5 protrudes.

The sliding body 7 comprises an inner channel 60 for insertion of a reference pin 15 adapted to be fixed to the bone B in order to guide the instrument 1 during cutting. The channel 60 extends through the sliding body 7 and is continued by a channel 92 provided in the handle 9. A front portion 94 of the handle 9 is inserted through a bore 52b of the pin 52. The entire instrument 1 is therefore free to translate axially with respect to the reference pin 15 during cutting.

The reference pin 15 and the instrument 1 form a surgical bone preparation assembly. The assembly may also include a non-shown tool for positioning or guiding the reference pin 15 on the bone B. This tool may be patient specific and built to correspond to the bone supports of the patient. The shape of the tool may be obtained with a planning software.

The working principle of the invention will now be explained in detail with reference to FIGS. 6, 7, 8 and 9. In a first configuration represented on FIGS. 6 and 8, the instrument 1 is positioned away from the bone B before the beginning of the cutting operation. The instrument 1 is mounted on the reference pin 15. The control ring 11 is maneuvered to set the cutting depth to the maximal value or another value by rotating the control ring 11 and releasing it. Under action of the spring 13, the notch 114a associated with the maximal cutting depth is inserted on the protrusion 74. The maximal cutting depth is marked by a marking "4" on the outer surface of the control ring 1. In this configuration, the main body 5 is completely pushed forward by the spring 13. The protrusion 52a is therefore located away from the surface 110, and the contacting surface 50 protrudes from the blades 32 of the cutting element 3.

When cutting begins, the instrument 1 is pushed along the axis X towards the bone B and is guided by the reference pin 15. The contacting surface 50 abuts against the bone B, and the instrument 1 is pushed further towards the bone B so that the cutting element 3 cuts the bone B around the contacting surface 50. The sliding body 7 therefore translates with respect to the main body 5, the spring 13 is compressed and the pin 52 is moved with respect to the sliding body 7 towards the proximal side, in the direction of the surface 110. The movement of the pin 52 is allowed by the free space provided by the oblong hole 70.

Figures 9, 10:
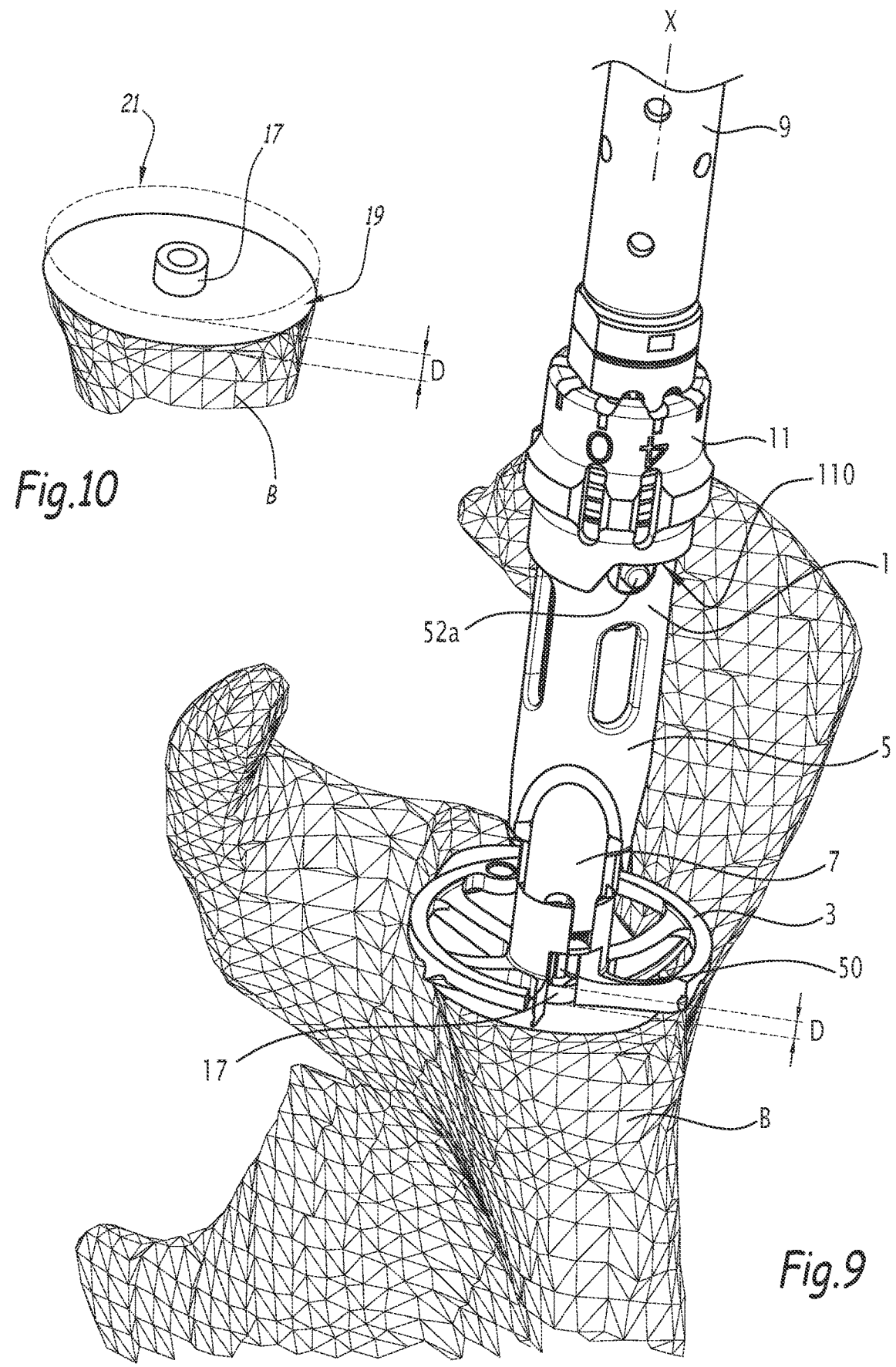
FIG. 9 is a view similar to FIG. 8, at the end of the cutting step.
FIG. 10 is a perspective view of the bone at the end of the cutting step.

As represented on FIGS. 7 and 9, once the desired cutting depth D is obtained, the protrusion 52a abuts against the surface 110, preventing the sliding body 7 from translating further with respect to the main body 5. The surface of the bone B has been reamed, leaving a bone remain 17 having the shape of the inner space 30 of the cutting element 3. The height extending between the reamed surface 19 and the former bone surface 21, that is represented in dotted lines on FIG. 10 and is present on the bone remain 17, corresponds to the cutting depth D.

The cutting depth is preferably pre-planned, for example using imaging such as X-rays, MM or CT scans, and/or using a pre-planning software for visualizing the bone in three dimensions. The software used for providing a tool for positioning the reference pin 15 may be used.

According to an optional embodiment, the sliding body 7 can be dismounted from the main body 5. The handle 9 can be separated from the sliding body 7 by unscrewing. With the front portion 94 being extracted from the bore 52b, the pin 52 can be radially removed from the sliding body 7. The sliding body 7 can then be axially dismounted from the main body 5.

Figure 11:
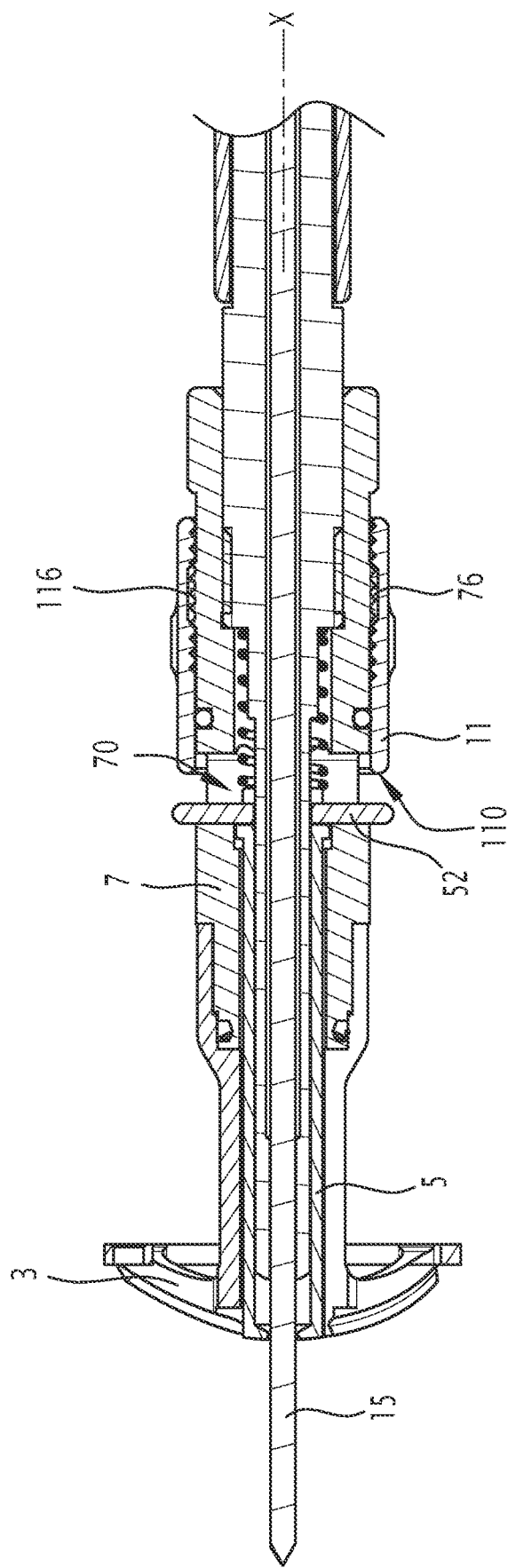
FIG. 11 is a sectional view of a surgical bone preparation instrument according to a second embodiment of the invention, along a longitudinal plane comprising a central axis of the instrument.

A second embodiment of the invention is represented on FIG. 11. In this embodiment, elements similar to the embodiments of FIGS. 1 to 9 have the same references and work in the same way.

In the embodiment of FIG. 11, the control ring 11 comprises an inner thread 116 and the sliding body 7 comprises an outer thread 76. The control ring 11 is mounted on the sliding body 7 with a screw mounting. By unscrewing or screwing the control ring on the sliding body 7, the axial position of the control ring 11 on the sliding body 7 can be adjusted. The screwing or unscrewing for adjusting the position of the control ring 11 can be easily made in a single movement with two fingers, in a single action.

The abutment surface 110 is, in this case, perpendicular to the central axis X, and the cutting depth is adjusted by modifying the axial position of the control ring 11 instead of modifying the angular position of the control ring in the first embodiment.

In a similar principle, the instrument of FIG. 11 comprises a radial pin 52 that is mounted fixed in translation with respect to the main body 5, and free to translate in an oblong hole 70 of the sliding body 7. When the desired cutting depth is reached, the pin 52 abuts against the surface 110, preventing the instrument from reaming the bone B to a depth superior to the adjusted depth.

The invention also concerns a surgical articulation replacement method, comprising at least a step consisting of making a bone preparation with a surgical bone preparation instrument, said bone preparation consisting of making a cut of a specific required cutting depth, wherein the specific required cutting depth of the bone preparation is pre-planned.

The invention also concerns a surgical articulation replacement method, in which the specific required cutting depth of the bone preparation is pre-planned using a pre-planning software.

What is claimed is:

1. Surgical bone preparation instrument comprising a main body terminated by a contacting surface adapted to abut on a bone and to remain stationary thereon, and a sliding body equipped with a cutting element, wherein the cutting element and sliding body are movable in translation, axially along a central axis of the bone preparation instrument, with respect to the main body and the contacting surface when the main body stationarily abuts the bone through the contacting surface, wherein the bone preparation instrument includes a cutting depth control ring that is separate from the main body and the sliding body, wherein the cutting depth control ring forms an abutment surface against the movement of one of the main body and the sliding body when the sliding body reaches an adjusted cutting depth corresponding to an adjustment position of the control ring, wherein the abutment surface has a substantially helical profile defining increasing cutting depths.

2. Surgical bone preparation instrument according to claim 1, wherein the cutting depth is adjusted by rotating the control ring to adjust an axial position of the helical profile of the abutment surface of the control ring with respect to the sliding body.

3. Surgical bone preparation instrument according to claim 1, wherein the cutting depth control ring is adjustable by a single action.

4. Surgical bone preparation instrument according to claim 1, wherein the main body comprises a radial pin extending in an oblong hole of the sliding body, the abutment surface of the cutting depth control ring acting as an axial stop on the radial pin.

5. Surgical bone preparation instrument according to claim 1, wherein the control ring comprises markings for checking the position of the control ring.

6. Surgical bone preparation instrument according to claim 1, wherein:

the cutting depth control ring is mounted on the sliding body with a screw mounting, and the cutting depth is adjusted by screwing or unscrewing the control ring to adjust its axial position on the sliding body.

7. Surgical bone preparation instrument according to claim 1, wherein:

the cutting depth control ring is mounted movable in rotation and fixed in translation on the sliding body and spring-biased by a spring with respect to the main body along the central axis of the surgical bone preparation instrument, and the abutment surface of the cutting depth control ring has a profile defining different axial lengths of the cutting depth control ring.

8. Surgical bone preparation instrument according to claim 7, wherein the spring urges the contacting surface of the main body against the bone during cutting.

9. Surgical bone preparation instrument according to claim 7, wherein:

the cutting depth control ring comprises a proximal axial surface having notches distributed circumferentially for positioning according to various depths corresponding to the different axial lengths of the control ring, and the sliding body comprises a protrusion adapted to insert in the notches of the proximal axial surface to lock an angular position of the control ring under action of the spring.

10. Surgical bone preparation instrument according to claim 7, wherein the sliding body is arranged radially inside a cylindrical portion of the main body, wherein the contacting surface of the main body is arranged radially inside the cutting element, and wherein the sliding body comprises longitudinal slits receiving in sliding manner attachment members of the main body which connect the contacting surface to the cylindrical portion.

11. Surgical bone preparation instrument according to claim 1, wherein the cutting element comprises a central aperture through which the contacting surface of the main body protrudes.

12. Surgical bone preparation instrument according to claim 1, wherein the sliding body can be dismounted from the main body.

13. Surgical bone preparation instrument according to claim 1, wherein the adjusted cutting depth is pre-planned.

14. Surgical bone preparation instrument according to claim 1, wherein the main body and the sliding body comprise a bore for insertion of a reference pin adapted to be fixed to the bone in order to guide the bone preparation instrument.

15. Surgical bone preparation assembly comprising the surgical bone preparation instrument according to claim 1, wherein the surgical bone preparation assembly comprises a patient-specific positioning tool for positioning at least one reference pin on the bone.

* * * * *